United States Patent [19]

Valenti

[11] 4,104,468

[45] Aug. 1, 1978

[54] 1,3,4-OXADIAZOLYL-(2)-VINYL STILBENE OPTICAL BRIGHTENERS

[75] Inventor: Salvatore Valenti, Bottmingen, Switzerland

[73] Assignee: Sandoz Ltd., Basel, Switzerland

[21] Appl. No.: 735,797

[22] Filed: Oct. 26, 1976

[30] Foreign Application Priority Data

Oct. 28, 1975 [CH] Switzerland .................. 13938/75

[51] Int. Cl.² .................................. C07D 271/10
[52] U.S. Cl. ........................... 542/447; 8/1 W; 252/8.6; 252/301.24; 542/459
[58] Field of Search .................. 260/240 CA, 240 D; 542/447

[56] References Cited

U.S. PATENT DOCUMENTS 3,947,410  3/1976  Meyer ..................... 260/240 CA

OTHER PUBLICATIONS

Naboikin et al., Chemical Abstracts, 73(1970), #93494.

Primary Examiner—Arthur P. Demers
Attorney, Agent, or Firm—Gerald D. Sharkin; Richard E. Vila; Thomas C. Doyle

[57] ABSTRACT

The present invention relates to optical brightening agents comprising the basic structure of formula I,

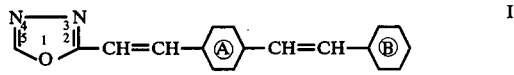

The brighteners are useful for optically brightening textile and non-textile substrates, e.g. of natural or regenerated cellulose, natural or synthetic polyamides, modified or non-modified polyolefins, polyurethanes, polyvinyl chloride and polyester.

21 Claims, No Drawings

1,3,4-OXADIAZOLYL-(2)-VINYL STILBENE OPTICAL BRIGHTENERS

IMPROVEMENTS IN OR RELATING TO ORGANIC COMPOUNDS

The invention relates to stilbene derivatives.

The invention provides optical brightening agents comprising the basic structure of formula I,

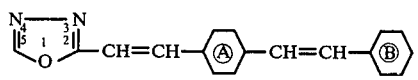
I

The oxadiazole group may be unsubstituted or substituted in the 5-position by a substituent conventional in optical brighteners of the 1,3,4-oxadiazolyl-(2)-vinyl series and rings A and B may be substituted by non-chromophoric substituents, ring A conveniently being unsubstituted or substituted by, e.g. a single, substituent(s) conventional in phenylene bridging groups in optical brighteners, ring B, similarly, conveniently being unsubstituted or substituted by, e.g. one or two, substituents conventional in optical brighteners of the styryl series and optionally having a 5- or 6-membered ring, e.g. a methylenedioxy or benzene ring, fused thereto.

As will be appreciated, the present invention is based on the discovery of the structure of formula I, above, and its eminent suitability as forming the basic structure of optical brightening agents. The selection of appropriate substituents, having regard to the known general effects of such substituents and the desired particular use of the optical brighteners, is within the skill of the man in the art.

Of particular interest are compounds having the basic structure of formula I, in which one of the substituents on ring A and/or B is a second order, i.e. electron withdrawing, substituent (other than phenyl) e.g. such as hereinafter described. It being especially preferred to have one of such substituents on ring B where it has a hypsochromic effect and a more or less pronounced intensifying effect, depending on position, on the fluorescence of the compounds.

The preferred compounds of the invention are the compounds of formula I'',

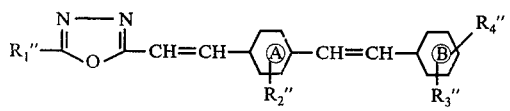
I'' wherein
  $R_1''$ is diphenylyl or phenoxyphenyl, each unsubstituted or mono-substituted by —SO$_3$M; or phenyl, unsubstituted or substituted by up to 3 substituents selected from C$_{1-4}$-alkyl, C$_{1-4}$alkoxy, chlorine, cyano, —COOR', —CONR''R''', —SO$_3$M and —SO$_2$R$^{iv}$, with the proviso that not more than one substituent is selected from the group cyano, —COOR', —CONR''R''', —SO$_3$M and —SO$_2$R$^{iv}$,
  $R_2''$ is hydrogen, cyano, —COOR', —CONR''R''', —SO$_2$R$^{iv}$ or —SO$_3$M,
either
  $R_3''$ and $R_4''$, independently of one another and independently of $R_2''$, each have one of the significances of $R_2''$, or
  $R_3''$ and $R_4''$ are in ortho relative positions, one to another, and form a fused benzene ring,
  R'' is hydrogen or C$_{1-4}$alkyl, preferably hydrogen,
  R$^{iv}$ is C$_{1-4}$alkyl; or phenyl, unsubstituted or substituted by up to 3 substituents selected from C$_{1-4}$alkyl, C$_{1-4}$alkoxy, chlorine and —SO$_3$M, with the proviso that no more than one —SO$_3$M group is borne thereby, preferably C$_{1-4}$alkyl; or phenyl, unsubstituted or mono-substituted by methyl; more preferably C$_{1-4}$alkyl,
  R', independently from R$^{iv}$, is M or one of the significances of R$^{iv}$, preferably hydrogen or C$_{1-4}$alkyl,
  R''', independently from R$^{iv}$, is hydrogen or one of the significances of R$^{iv}$, preferably hydrogen, and
  M is hydrogen or a non-chromophoric cation, with the proviso that, at most, two of the substituents $R_2''$, $R_3''$ and $R_4''$ signify substituents selected from cyano, —COOR', —CONR''R''', —SO$_2$R$^{iv}$ and —SO$_3$M.

In the compounds of formula I'' preferably not more than two substituents are present as $R_2''$, $R_3''$ or $R_4''$ or contained in $R_1''$, selected from cyano, —COOR', —CONR''R''', —SO$_2$R$^{iv}$ and —SO$_3$M (i.e. so-called "second order" substituents). Ring B is preferably substituted by not more than one of said second order substituents and, where one of said substituents is present, it is preferably in ortho position to the —CH=CH— group.

Those compounds of formula I'' are preferred where a maximum of one of $R_2''$, $R_3''$ and $R_4''$ signifies a second order substituent, the other two thereof preferably being hydrogen.

Where $R_1''$ is substituted phenyl (other than diphenyl or phenoxyphenyl), the preferred substituents are chlorine, C$_{1-4}$alkyl, C$_{1-4}$alkoxy, —COOR' (of which alkoxy(C$_{1-4}$)carbonyl and —COOM are preferred), cyano and —SO$_3$M, especially chlorine, C$_{1-4}$alkyl and C$_{1-4}$alkoxy, it preferably being mono-substituted phenyl.

Where $R_1''$ is diphenylyl or phenoxyphenyl, mono-substituted by —SO$_3$M, the —SO$_3$M group is preferably on the ring remote from the oxadiazole ring.

The preferred significances of $R_1''$ are phenyl, unsubstituted or mono-substituted by chlorine, C$_{1-4}$alkyl, C$_{1-4}$alkoxy, alkoxy(C$_{1-4}$)carbonyl, —COOM, cyano, sulpho, phenyl, monosulphophenyl, phenoxy or monosubphophenoxy, the more preferred significances being phenyl, unsubstituted or monosubstituted by chlorine, C$_{1-4}$alkyl or C$_{1-4}$alkoxy, the most preferred significance being unsubstituted phenyl.

The preferred significances of $R_2''$, $R_3''$ and $R_4''$, independently, are hydrogen, cyano, alkoxy(C$_{1-4}$)carbonyl, —COOM, —CONH$_2$, C$_{1-4}$alkylsulphonyl and —SO$_3$M. More preferably either one of $R_2''$, $R_3''$ and $R_4''$ is cyano, alkoxy(C$_{1-4}$)carbonyl, —CONH$_2$, —COOM, C$_{1-4}$alkylsulphonyl or —SO$_3$M and the other two hydrogen. Still more preferably either one of $R_2''$, $R_3''$ and $R_4''$ is cyano, alkoxy(C$_{1-4}$carbonyl or —COOM, and the other two hydrogen, or $R_4''$ is C$_{1-4}$alkylsulphonyl and $R_2''$ and $R_3''$ are both hydrogen.

As a preferred class of compounds of formula I'' may be given the compounds of formula I''',

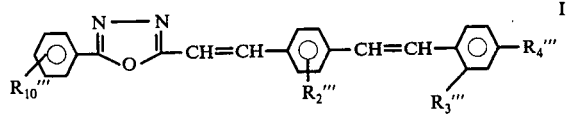

where
one of $R_2'''$, $R_3''''$ and $R_4''''$ is cyano, alkoxy($C_{1-4}$)carbonyl, —$CONH_2$, —COOM, $C_{1-4}$alkylsulphonyl, or —$SO_3M$ and the other two hydrogen, and $R_{10}''''$ is hydrogen; chlorine; $C_{1-4}$alkyl; $C_{1-4}$alkoxy; alkoxy($C_{1-4}$) carbonyl; —COOM; cyano; sulpho; phenyl, unsubstituted or mono-substituted by —$SO_3M$; or phenoxy, unsubstituted or mono-substituted by —$SO_3M$.

As a still further preferred class may be given the compounds of formula I''', wherein $R_{10}'''$ is hydrogen, chlorine, $C_{1-4}$alkyl or $C_{1-4}$alkoxy, especially hydrogen, and either one of $R_2'''$, $R_3'''$ and $R_4'''$ is cyano, alkoxy($C_{1-4}$)carbonyl or —COOM, and the other two hydrogen, or $R_4'''$ is $C_{1-4}$alkylsulphonyl and $R_2'''$ and $R_3'''$ are hydrogen.

In any —COOM group in the compounds of the invention, M is preferably hydrogen, particularly where the compounds are free from —$SO_3M$ groups.

Where M in the compounds of formulae I'' and I''' is a non-chromophoric cation, the exact nature thereof is not critical. The preferred cations are those conventional in the anionic optical brightener art, such as alkali metal cations, e.g. of lithium, potassium and sodium, alkaline-earth metal cations, e.g. of magnesium, the ammonium cations, such as of formula $N(R)_4$, where the R's, independently, are hydrogen, $C_{1-4}$alkyl or $C_{2-3}$hydroxyalkyl, with the proviso that when one R is $C_{2-3}$ hydroxyalkyl, at least one R is hydrogen, e.g. mono-, di- or tri-ethanolammonium and mono-, di- and triisopropanolammonium cations, and the pyridinium cation. The most preferred cation is the sodium cation.

The invention also provides a process for the production of the compounds having the basic structure of formula I, which process comprises a. reacting a corresponding compound of formula II,

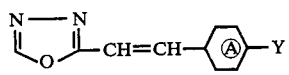

with a corresponding compound of formula III,

one of Y and $Y_2$ being an aldehyde group or a functional derivative thereof, the other being methyl, carboxymethyl, a functional derivative of carboxymethyl, or a group of formula,

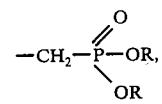

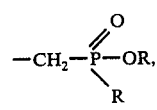

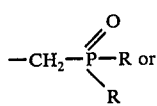

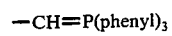

where R is $C_{1-5}$alkyl or phenyl, or b. reacting a corresponding compound of formula IV,

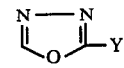

with a corresponding compound of formula V,

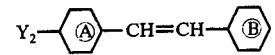

where Y and $Y_2$ are as defined above.

The above reactions may be carried out in conventional manner for the types of reactions involved.

As will be appreciated, the compounds of formulae II, III, IV and V may be substituted depending on the desired substitution in the final compounds. They are either known or may be obtained in analogous manner to the known compounds.

The resulting compounds of the invention may be isolated and purified in conventional manner. As will be appreciated, interconversion from one compound of the invention to another, e.g. by conversion of carboxylic or sulphonic acid groups therein to the corresponding amides and esters, by sulphonation to introduce sulphonic acid groups, by replacement of bromo substituents by cyano, e.g. using Copper (I) cyanate, and by hydrolysis of cyano groups to amide groups, may be carried out as desired.

The compounds of the invention may be employed for the optical brightening of a wide variety of substrates, both textile and non-textile, e.g. of natural or regenerated cellulose, natural or synthetic polyamides, modified or non-modified polyolefines, polyurethanes, polyvinyl chloride and polyester. The compounds containing sulpho groups are particularly suitable for the brightening of hydrophilic substrates, e.g. of natural or regenerated cellulose, natural or synthetic polyamides, basic modified polypropylene and polyurethane. The compounds free from sulpho groups are more suitable for the brightening of synthetic polyamide, polyolefine, polyvinyl chloride and especially polyester, for which last mentioned substrate it is especially preferred to employ compounds of formula I''', wherein $R_{10}'''$ is hydrogen, chlorine, $C_{1-4}$alkyl or $C_{1-4}$alkoxy and wherein either one of $R_2'''$, $R_3'''$ and $R_4'''$ is cyano, $C_{1-4}$alkoxycarbonyl or carboxy and the other two hydrogen, or $R_4'''$ is $C_{1-4}$ alkylsulphonyl and $R_2'''$ and $R_3'''$ are hydrogen. If desired, e.g. where the substrate comprises both hydrophobic and hydrophilic material, e.g. blends, a mixture of sulpho-group containing brightener with sulphogroup free brightener can be employed, either both of said brighteners or only one of said brighteners being of the present invention. In this case, where only one of said brightener is of the present invention, such brightener is preferably the sulpho group free brightener.

The substrates to be brightened may be in any desired form, e.g. loose fibre, filament, thread, woven, knit, non-woven, semi-finished, fully finished, moulded, (e.g. film), non-moulded (e.g. chip) or molten (e.g. polyester spin mass) form. The brightener may also be added to polymer precursors, etc.

Conventional methods of application may be employed, e.g. exhaust, padding (e.g. thermosol, acid shock and high temperature), printing, stock addition, and surface treatment, e.g. in paper sizing and in synthetic resin finishing processes, conventional amounts of the brightener, e.g. 0.001 to 1.0%, preferably 0.005 to 0.5%, and more, preferably 0.02 to 0.05%, based on the weight of the substrate, being used. As will be appreciated the method of application will depend on the nature of the substrate and on the type of brightener, e.g. sulpho-containing or sulpho-free, employed.

Particular preference is given to the brightening of polyester fibre material employing sulpho-group free brighteners from an aqueous dispersion. Such compounds, however, may also be applied from solutions in organic solvents.

The brightener may be employed alone or along with such conventional aids and additives as bleaching agents, washing agents, softeners, carriers and dispersion aids.

They may be applied in mixtures one with another and with other brightening agents. Of particular interest is the application of compounds of the present invention having a neutral-blue to greenish-blue fluorescence, especially such compounds of formula I'', wherein up to one second order substituent is present in ring B, along with brighteners having a reddish to violet-blue fluorescence. Such latter brighteners may be of the present invention or may be other brighteners, e.g. a brightener disclosed in French Pat. Nos. 1,322,849 or 1,266,688, in Swiss Pat. No. 333,183 or in Japanase Patent Publication No. 71-13953. Such combinations enable higher and more brilliant whitening effects to be achieved, especially with the sulpho-group free compounds.

The invention is illustrated by the following Examples, in which all parts and percentages, unless otherwise stated, are by weight and all temperatures are in degrees Centigrade.

EXAMPLE 1

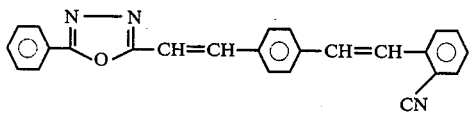

6

16.7 Parts of the compound of formula

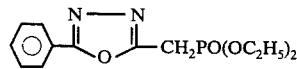

(7)

and 10.7 parts of the compound of formula

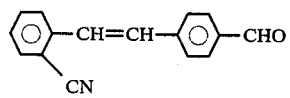

(8)

are suspended with stirring in 47 parts of dimethyl formamide, with nitrogen being passed through, and then a freshly produced solution of 2 parts of sodium in 32.5 parts by volume of methanol is slowly added at room temperature. The resultant brown suspension is then stirred for 4 hours at 40°–45°, then cooled and poured into ice water. The deposit is suctioned off, washed firstly with water, then with methanol and dried. By recrystallisation from terpene aline the compound of formula (6) is obtained as a bright yellow powder having MP 200°–201°. The solutions of the product of formula 6 is chlorobenzene fluoresce in a strong blue colour.

The product of formula 7 which is required for synthesis is produced by reacting 2-phenyl-5-chloromethyl-1,3,4-oxadiazole (Belgian Pat. No. 773,033) with excess triethyl phosphite at 140°–150° for 3–4 hours. The excess triethyl phosphite is removed by vacuum distillation and the residue as such is further reacted.

The compound of formula 8 may be obtained as follows: 70 parts of the compound of formula

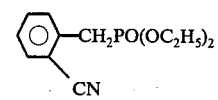

9

(prepared from o-cyanobenzyl bromide and triethyl phosphite as described previously) are dissolved in 440 parts by volume of dimethyl formamide, and a freshly produced solution of 6.9 parts of sodium in 110 parts by volume of methanol is added over the course of 15 minutes with stirring and with nitrogen being passed through. Then, 33.2 parts of p-toluyl aldehyde are added in drops, and this is stirred firstly for 1 hour at room temperature, and then for 4 hours at 40°–45°.

The reaction mixture is then cooled and poured into ice water. The deposit is suctioned off, washed with water and dried.

The compound of formula

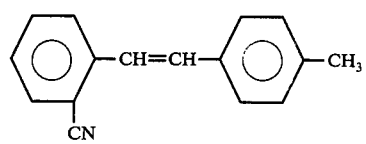

10 which is further reacted without purification is obtained. MP = 60°-1° (from ethanol). 80 parts of the compound of formula 10, 65 parts of N-bromosuccinimide and 0.7 parts of dibenzoyl peroxide in 750 parts by volume of carbon tetrachloride are heated with stirring for 12 hours at reflux. The reaction mixture is then filtered off whilst hot, and the filtrate is purified by a solution of 75 parts of hexamethylenetetramine in 420 parts by volume of chloroform, and then boiled for a short time (about 15-30 minutes). The reaction matter is then cooled, the deposit is suctioned off, absorbed in 720 parts of water, then 720 parts by volume of glacial acetic acid and 21.7 parts hexamethylenetetramine are added, and it is boiled for 2 hours at reflux. After cooling, the suspension is suctioned off, the deposit is washed with water and dried. By recrystallisation from terpene aline (White Spirit), the compound of formula 8 having MP = 151°–2° is obtained.

The compounds of formula 6',

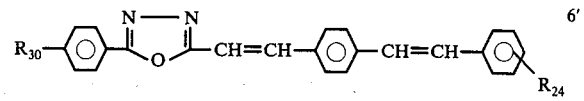

6' can be produced analogously to the compound of formula 6, wherein the symbols $R_{30}$ and $R_{24}$ have the meanings shown in the following table.

| Example | $R_{30}$ | $R_{24}$ | Fluorescent colour in chlorobenzene |
|---|---|---|---|
| 1a | —CH$_3$ | o-CN | blue |
| 1b | —CH$_3$ | —CN | " |
| 1c | —CH$_3$ | p-CN | " |
| 1d | —H | m-CN | " |
| 1e | —H | p-CN | " |
| 1f | —OCH$_3$ | o-CN | " |
| 1g | —OCH$_3$ | m-CN | " |
| 1h | —C(CH$_3$)$_3$ | o-CN | " |
| 1i | —C(CH$_3$)$_3$ | p-CN | " |
| 1j |  | H | " |
| 1k | —CN | H | " |
| 1l | —H | p-SO$_2$CH$_3$ | " |
| 1m | —H | p-SO$_2$— | " |

Furthermore the compounds of formula I',

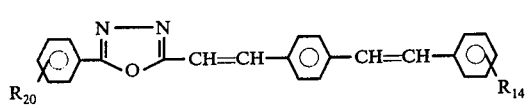

can also be produced analogously to the compound of formula 6 wherein the symbols $R_{20}$ and $R_{14}$ have the meanings shown in the following Table.

| Example | $R_{20}$ | $R_{14}$ | Fluorescent colour in chlorobenzene |
|---|---|---|---|
| 1n | o-CH$_3$ | H | blue |
| 1o | p-CH$_3$ | H | blue |
| 1p | p-C(CH$_3$)$_3$ | H | blue |
| 1q | p-OCH$_3$ | H | greenish-blue |
| 1r | H | p-CH$_3$ | blue |
| 1s | H | p-OCH$_3$ | greenish-blue |
| 1t | H | o-CH$_3$ | blue |
| 1u | H | o-OCH$_3$ | greenish-blue |
| 1v | p-CH$_3$ | H | blue |
| 1w | H | H | blue |

EXAMPLE 2

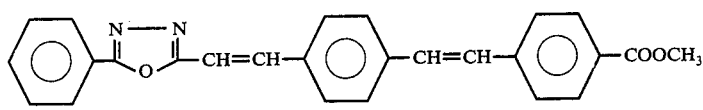

19.7 parts of 2-phenyl-5-chloromethyl-1,3,4-oxadiazole and 27.6 parts of triphenylphosphine in 680 parts by volume of dimethyl formamide are heated with stirring for 3 hours at 80 - 85° with nitrogen being passed through. Heating is then stopped, 27.6 parts of the compound of formula

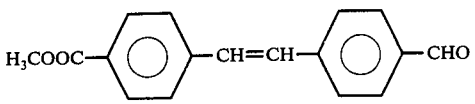

are added to the reaction mixture, and it is cooled to room temperature. Then, a newly produced solution of 2,4 parts of sodium in 60 parts by volume of methanol is slowly added in drops, whereby a deep yellow deposit becomes visible. The reaction mixture is further stirred for 4 hours at room temperature, then suctioned off, the deposit is washed with water and dried. By recrystallisation from chlorobenzene, the compound of formula 11 is obtained in pure form as pale yellow, silvery crystals having MP = 232°-3°. The solution in chlorobenzene fluoresce in a strong blue violet colour.

The compound of formula 12 may be obtained from the compound of formula

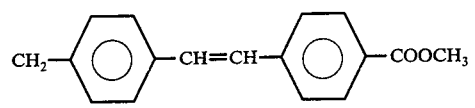

analogously to the compound of formula 8 by brominating the methyl group with N-bromosuccinimide and reacting the bromomethyl derivative with hexamethylene tetra-amine, following the teaching of Sommelet.

The compounds of formula

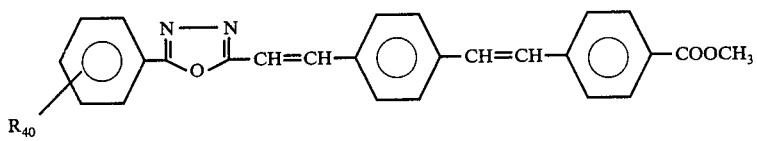

may be obtained analogously to the compound of formula 11, wherein the symbol $R_{40}$ has the meanings shown in the following table.

| Example | $R_{40}$ | Fluorescent colour in chlorobenzene |
|---|---|---|
| 2a | o-CH$_3$ | blue |
| 2b | p-CH$_3$ | " |
| 2c | p-C(CH$_3$)$_3$ | " |
| 2d | p-OCH$_3$ | greenish-blue |

EXAMPLE 3

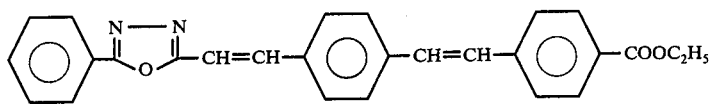

21 Parts of the compound of formula

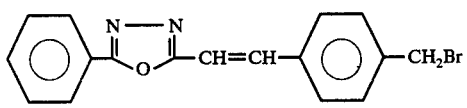

and 16.8 parts triphenylphosphine in 400 parts by volume of dimethylformamide are heated with stirring for 3 hours at 80°–85°. The mixture is cooled and 10.7 parts of p-formylbenzoic acid ethyl ester are added. At room temperature a solution of 1.5 parts of sodium in 60 parts by volume of ethanol is slowly added dropwise, then further stirred for 4 hours at room temperature.

The reaction mixture is poured into ice water with stirring. The deposit is suctioned off, washed with water and dried.

EXAMPLE 4

In place of the p-formylbenzoic acid ethyl ester in Example 3, by using equivalent amounts of α-naphthyl aldehyde, or β-naphthyl aldehyde or bi-phenyl aldehyde, the compounds of formula By subjecting the cyano compound of formula 19 to acid hydrolysis in conventional manner the corresponding aminocarbonyl compound of formula 19a may be obtained

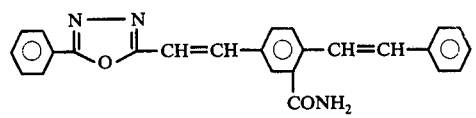

The compound of formula 20 can be obtained by the Wittig reaction from benzaldehyde and

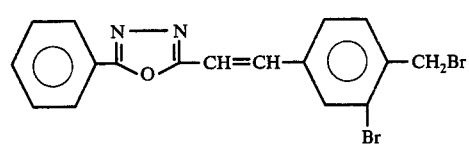

and following to the procedure for the compound of formula 14.

| | | Fluorescent colour in chlorobenzene |
|---|---|---|
| 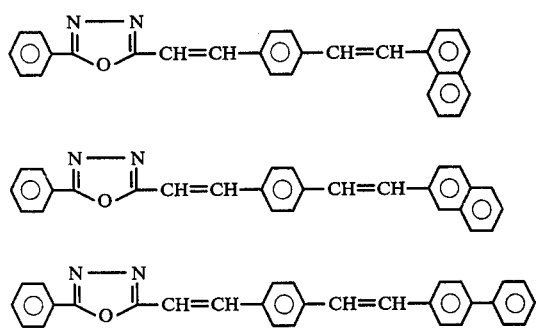 | 16 | greenish blue |
| | 17 | greenish blue |
| | 18 | green-blue | can be obtained.

EXAMPLE 5

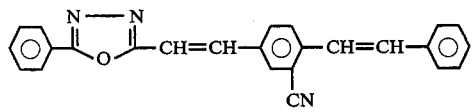

31.4 Parts of the compound of formula

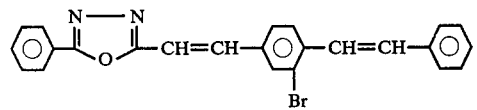

and 8.2 parts of copper-I-cyanide in 150 parts by volume of quinoline are stirred and boiled for 2 hours under reflux. The reaction mixture is poured with stirring into a solution of sodium cyanide and stirred further for 20 minutes at 60°–70°. The suspension is subsequently cooled, the deposit is suctioned off, washed with water and dried. By recrystallisation from chlorobenzene with the aid of bleaching earth, the compound of formula 19 is obtained having MP = 223°–26° and which fluoresce in chlorobenzene in a strong slight greenish-blue colour.

The compound of formula 21 may also be produced by the Wittig reaction from 2-phenyl-5-chloromethyl-1,3,4-oxadiazole and 3-bromo-4-methylbenzaldehyde and subsequently brominating with N-bromo succinamide.

EXAMPLE 6

31.4 Parts of the compound of formula

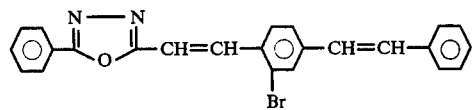

are reacted with 8.2 parts of copper-I-cyanide, similarly to the reaction given for the compound of formula 19, and the compound of formula

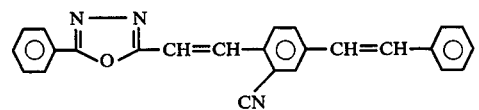

is obtained, which, when dissolved in chlorobenzene, has a strong greenish blue fluorescence.

The compound of formula 22 may be obtained by reacting 16.7 parts of the compound of formula 7 with 12.9 parts of the compound of formula

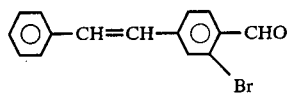
24 as described for the compound of formula 6. The compound of formula 24 may in turn be obtained as described for the compound of formula 10 by reacting 63.1 parts of diethylbenzyl phosphonate with 55.1 parts of 3-bromo-4-methylbenzyaldehyde, and then as described for the compound of formula 8 by converting the methyl group into the aldehyde group.

EXAMPLE 7

A suspension of 30 parts of sodium methylate in 60 parts by volume of dimethylformamide is gradually added in drops at 35°–40° over the course of 15 – 20 minute to a solution of 94.3 parts of the compound of formula

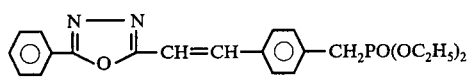
25 and 38 parts of o-carboxybenzaldehyde in 100 parts by volume of dimethyl formamide. Stirring continues for 10 minutes at room temperature and it is then cooled to 10° to 15°. Then, over the course of 30 minutes, 160 parts of ice water are added in drops at this temperature, the reaction mixture is poured into 2000 parts of ice water, and very slowly 1 N hydrochloric acid is added until a pH of 4 is reached, whereby the temperature is kept below 10°. After standing for several hours, the reaction product is filtered off, washed with water and dried. The compound of formula

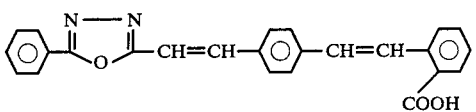
26 is obtained in a large quantity. After recrystallisation from chlorobenzene the compound of formula 26 melts at 225°–226° and in chlorobenzene solution has a blue fluorescence. The compound of formula 26 may also be reacted without recrystallisation to the corresponding ethylester as follows:

20 Parts of the compound of formula 26 are suspended in 400 parts by volume of o-xylene, reacted with 209.3 parts of triethylphosphite and stirred for 15 hours under reflux at the boil. The resulting solution is reduced under vacuum and the residue is purified from terpene aline (white spirit). The compound of formula

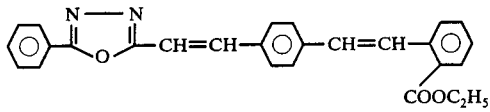
27 is obtained having MP = 154°–5°. When dissolved in chlorobenzene the compound of formula 27 has a very strong violet-blue fluorescence.

The compound of formula 25 may also be obtained from the compound of formula 15, by reacting it with triethyl phosphite, as described in Example 2.

EXAMPLE 8

A solution of 17.6 parts of the compound of formula 1 in 100 parts by volume of chlorosulphonic acid is stirred for 30 minutes at 70°, then cooled and applied to ice, whereby a yellow product is precipitated. This is suctioned off, washed with ice water and dried. The compound of formula

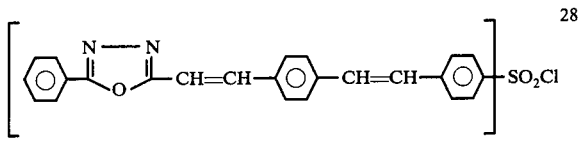
28 is obtained, and it is further reacted without further purification.

5 Parts of the compound of formula 28 are dissolved in the heat in 150 parts by volume of pyridine, then 20 parts of water are added in drops and are heated for 15 minutes at reflux. The reaction mixture is finally reduced under vacuum and the residue is recrystallised from n-butanol.

The compound of formula

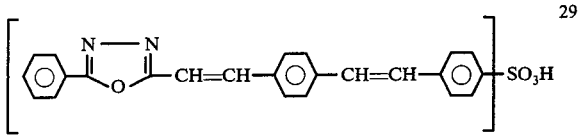
29 is obtained as a pyridinium salt.

EXAMPLE 9

39.3 Parts of the compound of formula 1w are entered with stirring at room temperature into 250 parts by volume of oleum 25%. The reaction mixture is stirred for 2 hours, then poured onto 500 parts of ice, whereby no solid product is precipitated. The mixture is neutralised in the heat with sodium acetate to a pH of 6 to 7, then cooled, the deposited salts are suctioned off and the filtrate is evaporated in a vacuum until dry. The compound of formula

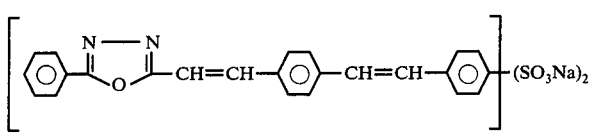
30 which still contains some sodium sulphate and sodium acetate is obtained.

The compound of formula 30 may be used for the brightening of polyamide and cellulose without additional purification.

The optical brighteners of the above Examples 1–7, in particular those of Examples 1, 2, 3 and 7 are very suitable for the use in combination with reddish brighteners, above all with the brighteners of the formulae

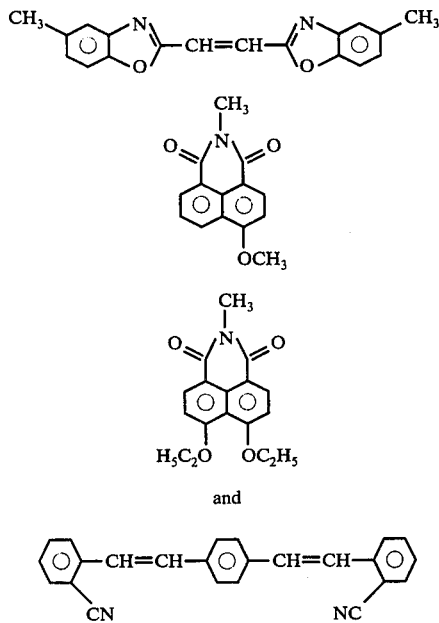

in particular for the use of optically brightening polyester.

Application Example A 2 parts of the compound of formula (6) are mixed with 2 parts of a high-sulphonated castor oil, 8 parts of dioctylphenylpolyglycol ether hydroxyacetic sodium, which contains 40 etheneoxy groups in the molecule, and 80 parts of water, and the mixture is processed in a comminuter, e.g. a sand mill, until the particle size is mainly 0.5–2 μ. 100 parts of a polyester fabric (polyethylene terephthalate) are entered at 50° into a bath having the following composition:

3000 parts of water
15 parts of a commercial carrier, e.g. ortho-dichlorobenzene,
2 parts of the above-described dispersion.

The bath is brought to boiling point over the course of 30 minutes, left for 45 minutes at boiling temperature with reflux and the fabric is subsequently treated at 70° in a bath containing 1.5 g/l of octylphenyl-decaglycol ether (volume of liquor 1:40, duration: 10 minutes). It is then removed, rinsed whilst warm and dried. The polyester fabric thus treated is considerably brightened. When working in closed apparatus at 120°–130°, similar whitening effects are obtained without adding a carrier.

Application Example B

A mixed fabric of cotton/polyester e.g. cotton-polyethylene terephthalate is impregnated at room temperature in a dye padder by liquor which contains, in 1000 parts of water, 20 parts of the dispersion of the optical brightener described in application example A. It is squeezed out to 80% liquid absorption, dried for 30 minutes at 60° and subjected to thermosol treatment for 1 minute at 200°. The fabric is considerably brightened in this manner and the effect is as strong as that described in application example A. Instead of the mixed fabric, if a pure polyester fabric is used ("Dacron", "Terylene", "Diolene" etc.), the thermosol treatment then taking place at temperatures of up to 220°, then this is brightened just as the mixed fabric.

Application Example C 100 parts of polyester fabric, e.g. polyethylene terephthalate, are treated for 1½ hours at 90°–95° in a bath containing 3000 parts of water, 6 parts of 85% formic acid, 6 parts of 80% sodium chlorite, 5 parts of a carrier, e.g. a trichlorobenzene mixture and 2 parts of the dispersion described in application example A. The fabric is subsequently washed, rinsed and dried. It then has a higher degree of whiteness than a comparable fabric which has been bleached under otherwise similar conditions, but without the addition of the compound of formula (6).

Application Example D 50 parts of polyester fabric are covered for a short time by a mixture consisting of 250 parts by volume of trichloroethylene and 250 parts by volume of chlorobenzene, in which 0.2 parts of the compound of formula (11) have been dissolved. The excess solvent is hydroextracted (about 100% solvent absorption) and the fabric is vacuum dried at 60° and subsequently treated for 15 minutes with steam at 120° to 130°. The polyester fabric thus treated has a considerably whiter appearance than the same fabric which is treated comparably as given above, but without the addition of the brightener. Instead of the polyester fabric, if a mixed fabric of cotton-polyester is used, e.g. cotton-diolene, similarly an effective brightening of the fabric is obtained.

Application Example E

In a stirring autoclave made of stainless steel, which has a descending cooler, are heated together 1000 parts of dimethylterephthalate, 665 parts of ethylene glycol, 0.55 parts of manganese acetate, 0.18 parts of antimony trioxide and 0.3 parts of the compound of formula 18 or 26. The methanol begins to split off at about 160° and this process lasts for 2½ hours. Towards the end, the temperature increases to about 225°. Then, 4 parts of titanium dioxide and 0.3 parts of phosphoric acid are added to the melt, the pressure in the reaction container is lowered to below 1 mm and the temperature is kept at 290° until the desired degree of polymerisation has been reached. The polymer thus obtained is spun into threads by known methods, with an excess pressure of 2–5 atmospheres (inert gas). The polyester threads obtained have a high degree of whiteness which is very fast to washing and to light.

Application Example F

100 Parts of polyester granulate are made into a powder in a mixing apparatus with 0.02 parts of the compound of formula 14, and they are subjected to the injection moulding process. The products obtained have an improved appearance as compared with those produced without the addition of the brightener. By replacing the polyester granulate in this example with granulates of other materials, e.g. polyamide, polystyrene, polyethylene or cellulose acetate, then similarly brightened products are obtained: the same applies when the compound of formula 27 is used instead of the compound of formula 14.

Application Example G

A polyamide fibre fabric (Perlon) is entered into a bath with a liquor ratio of 1:40 at 60°, the bath containing (in relation to the weight of the material) 0.1% of the brightener of formula 30, as well as per liter 1 g of 80% acetic acid and 0.25 g of an addition product of 30 to 35 mols of ethylene oxide on one mol of technical stearyl alcohol. It is heated over the course of 30 minutes to boiling temperature and is kept at boiling point for 30 minutes, After rinsing and drying, a strong brightening effect is obtained, with excellent fastness to light. Equally good brightening effects are obtained using a fabric of polyamide-66 (Nylon) instead of one of polyamide-6.

Finally, the procedure may be effected under high temperature conditions, e.g. for 30 minutes at 130°. For this type of application, the addition of 3 g/l of hydrosulphite to the liquor is recommended. Similar effects are obtained with the compound of formula 29 (pyridinium salt).

Application Example H

A bleached cotton material is entered into a bath with a liquor ratio of 1:25 at 20°, the bath containing (in relation to the weight of the material) 0.1 to 0.2% of the brightener of formula 30. This is heated over the course of 15 minutes to 50°, and then 5 g of crystalline sodium sulphate are added per liter of liquor. After a further 15 minutes, the fabric is rinsed for a short time, and subsequently dried. The cotton thus treated is whiter than fabric which has not been treated.

What is claimed is:

1. A compound useful as an optical brightener and having the formula

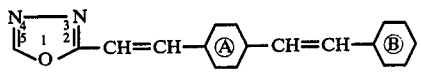

wherein the oxadiazole group is unsubstituted or substituted in the 5-position and the rings A and B are unsubstituted or substituted by non-chromophoric substituents.

2. A compound of formula I'',

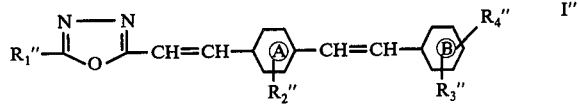

wherein
$R_1''$ is diphenylyl or phenoxyphenyl, each unsubstituted or mono-substituted by —$SO_3M$; or phenyl, unsubstituted or substituted by up to 3 substituents selected from $C_{1-4}$alkyl, $C_{1-4}$alkoxy, chlorine, cyano, —COOR', —CONR''R''', —$SO_3M$ and —$SO_2R^{iv}$, with the proviso that not more than one substituent is selected from the group cyano, —COOR', —CONR''R''', —$SO_3M$ and —$SO_2R^{iv}$,
$R_2''$ is hydrogen, cyano, —COOR', —CONR''R''', —$SO_2R^{iv}$ or —$SO_3M$,
either $R_3''$ and $R_4''$, independently of one another and independently of $R_2''$, each have one of the significances of $R_2''$,
or
$R_3''$ and $R_4''$ are in ortho relative positions, one to another, and form a fused benzene ring,
R'' is hydrogen or $C_{1-4}$alkyl, preferably hydrogen,
$R^{iv}$ is $C_{1-4}$alkyl; or phenyl, unsubstituted or substituted by up to 3 substituents selected from $C_{1-4}$alkyl, $C_{1-4}$alkoxy, chlorine and —$SO_3M$, with the proviso that no more than one —$SO_3M$ group is borne thereby, preferably $C_{1-4}$alkyl; or phenyl, unsubstituted or mono-substituted by methyl; more preferably $C_{1-4}$alkyl,
R', independently from $R^{iv}$, is M or one of the significances of $R^{iv}$, preferably hydrogen or $C_{1-4}$alkyl,
R''', independently from $R^{iv}$, is hydrogen or one of the significances of $R^{iv}$, preferably hydrogen, and
M is hydrogen or a non-chromophoric cation, with the proviso that, at most, two of the substituents $R_2''$, $R_3''$ and $R_4''$ signify substituents selected from cyano, —COOR', —CONR''R''', —$SO_2R^{iv}$ and —$SO_3M$.

3. A compound according to claim 2, in which a maximum of one of $R_2''$, $R_3''$ and $R_4''$ signifies a substituent selected from —CN, —COOR', —CONR''R''', —$SO_3M$ or $SO_2R^{iv}$ as defined in claim 2.

4. A compound according to claim 3, in which $R_1''$ is phenyl, unsubstituted or monosubstituted by chlorine, ($C_{1-4}$)alkyl, ($C_{1-4}$)alkoxy, alkoxy ($C_{1-4}$)carbonyl, —COOM, cyano, $SO_3M$, phenyl, phenyl monosubstituted by $SO_3M$, phenoxy or phenoxy monosubstituted by $SO_3M$.

5. A compound according to claim 4, in which one of $R_2''$, $R_3''$ and $R_4''$ is cyano, alkoxy($C_{1-4}$)carbonyl, —COOM, —$CONH_2$, ($C_{1-4}$) alkylsulphonyl or —$SO_3M$ and the other two are hydrogen.

6. A compound according to claim 2, of formula I'''

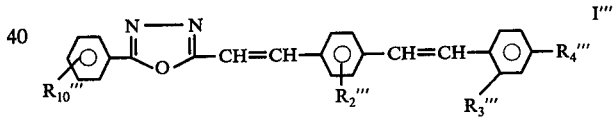

where
one of $R_2'''$, $R_3'''$ and $R_4'''$ is cyano, alkoxy($C_{1-4}$)carbonyl, —$CONH_2$, —COOM, $C_{1-4}$alkylsulphonyl, or —$SO_3M$ and the other two hydrogen, and
$R_{10}'''$ is hydrogen; chlorine; $C_{1-4}$alkyl; $C_{1-4}$alkoxy; alkoxy ($C_{1-4}$)carbonyl; —COOM; cyano; sulpho; phenyl, unsubstituted or mono-substituted by —$SO_3M$; or phenoxy, unsubstituted or mono-substituted by —$SO_3M$.

7. A compound according to claim 6, in which $R_{10}'''$ is hydrogen, chlorine, ($C_{1-4}$)alkyl or ($C_{1-4}$)alkoxy.

8. A compound according to claim 7, in which one of $R_2'''$, $R_3'''$ and $R_4'''$ is cyano, alkoxy ($C_{1-4}$)carbonyl or ≦COOM.

9. A compound according to claim 8, in which $R_{10}'''$ is hydrogen.

10. A compound according to claim 2, which is free from sulpho groups.

11. A compound according to claim 3, which contains one or two sulpho groups.

12. A compound according to claim 6, which is free from sulpho groups.

13. A compound according to claim 6, which contains one or two sulpho groups.

14. A compound according to claim 2, in which M is hydrogen or sodium.

15. A compound according to claim 14, in which M is hydrogen.

16. A compound according to claim 12, in which M is hydrogen.

17. A compound according to claim 12, of formula

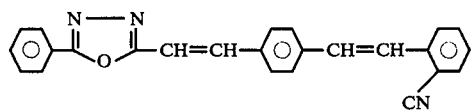

18. A compound according to claim 12, of formula

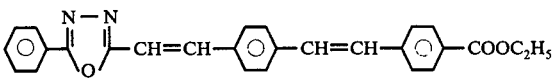

19. A compound according to claim 12, of formula

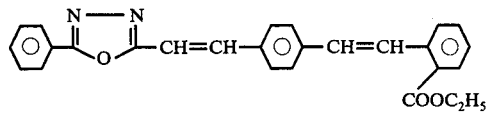

20. A compound according to claim 12, of formula

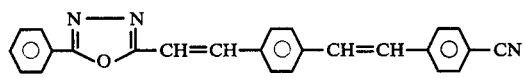

21. A compound according to claim 1 wherein the ring A is unsubstituted or monosubstituted and the ring B is unsubstituted or mono- or disubstituted and may have a methylenedioxy or fused benzene ring attached thereto.

* * * * *